United States Patent [19]
Mikus et al.

[11] Patent Number: 6,146,378
[45] Date of Patent: Nov. 14, 2000

[54] PLACEMENT GUIDE FOR ABLATION DEVICES

[75] Inventors: Paul W. Mikus; Jay J. Eum, both of Aliso Viejo, Calif.

[73] Assignee: Endocare, Inc., Irvine, Calif.

[21] Appl. No.: 09/272,889

[22] Filed: Mar. 19, 1999

[51] Int. Cl.[7] .................................................. A61B 18/18
[52] U.S. Cl. ............................... 606/21; 606/41; 607/113; 604/164.04; 604/164.09; 604/515; 600/585
[58] Field of Search ........................ 606/21, 41; 600/585, 600/104, 106, 117, 135; 604/164.01, 164.04, 164.07, 164.09, 164.11, 515; 607/105, 113

[56] References Cited

U.S. PATENT DOCUMENTS

| | | | |
|---|---|---|---|
| 5,390,661 | 2/1995 | Griffith et al. ............................ | 600/114 |
| 5,800,493 | 9/1998 | Stevens et al. .......................... | 607/113 |
| 5,873,815 | 2/1999 | Kerin et al. ............................... | 600/114 |
| 5,891,134 | 4/1999 | Goble et al. .............................. | 606/27 |
| 5,891,457 | 4/1999 | Neuwirth ................................. | 424/430 |
| 5,916,144 | 6/1999 | Li et al. .................................... | 604/515 |
| 5,935,098 | 8/1999 | Blaisdell et al. .......................... | 604/101 |

*Primary Examiner*—Linda C. M. Dvorak
*Assistant Examiner*—David M. Ruddy
*Attorney, Agent, or Firm*—Lyon & Lyon LLP

[57] ABSTRACT

A placement guide for positioning ablation devices within a human body is disclosed. The placement guide comprise an outer catheter and an inner tubular member disposed within a lumen of the outer catheter. When a stop on the inner tubular member engages a seat on the outer catheter, a distal projection of the inner tubular member extends from the distal end of the outer catheter. While monitoring the position of the inner tubular member through an endoscope inserted in its lumen, a clinician positions the distal projection within a human body for optimal ablation. After securing the outer catheter in position, the inner tubular member is withdrawn and replaced with an ablation device which is inserted distally within the outer catheter lumen until a stop on the ablation device engages the seat on the outer catheter wherein a distal projection of the ablation device extends from the distal end of the outer catheter. Because the distal projection of the inner tubular member has a length substantially identical to that of the inner tubular member, the ablation device may be positioned for optimal ablation.

10 Claims, 3 Drawing Sheets

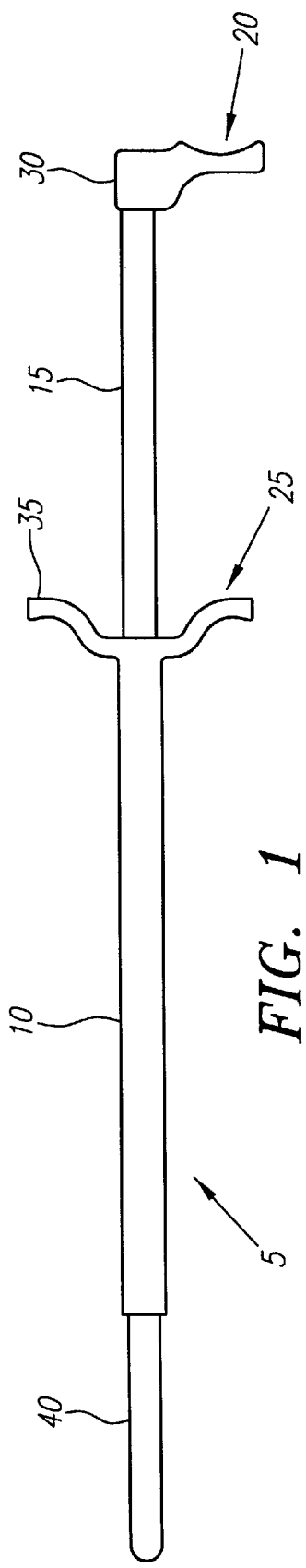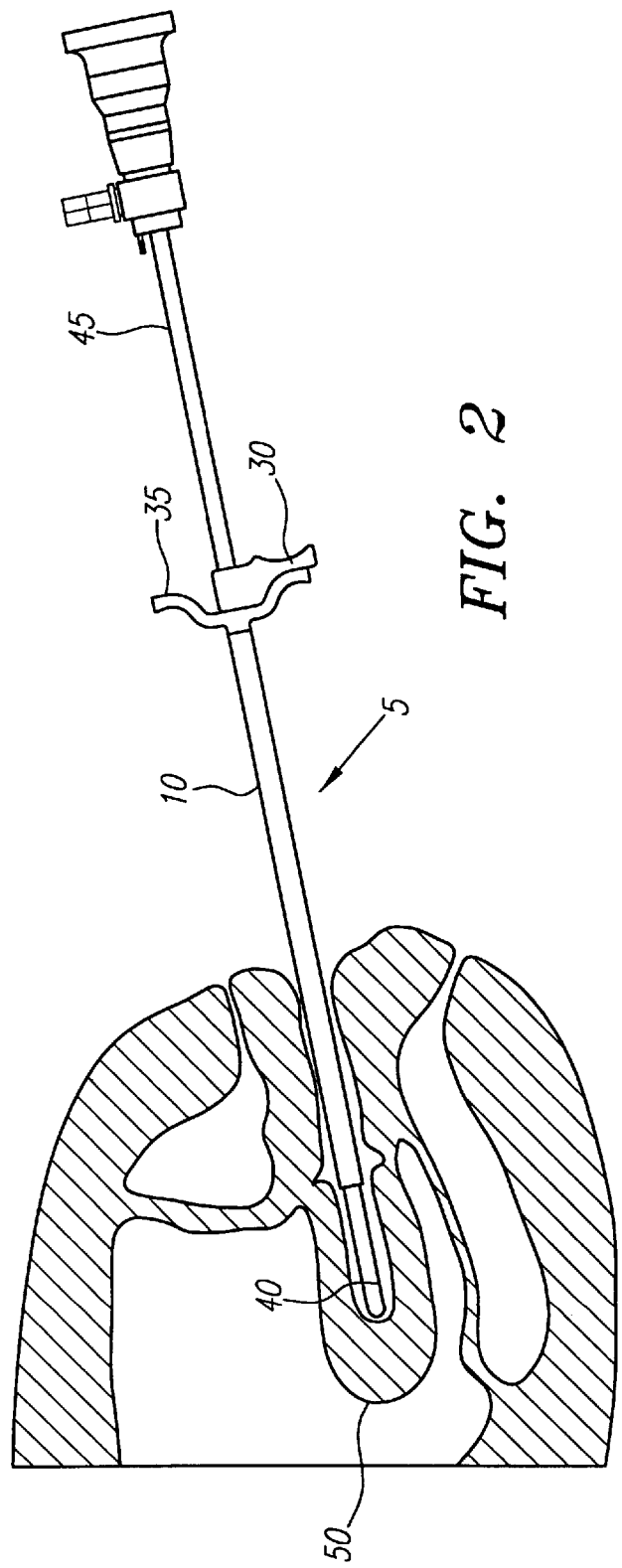

PLACEMENT GUIDE FOR ABLATION DEVICES

FIELD OF THE INVENTION

The present invention relates to placement guides for surgical ablation. In particular, the invention relates to a placement guide for an ablation device and to methods of endometrial ablation and other surgical procedures using the placement guide and ablation device.

BACKGROUND OF THE INVENTION

Cryosurgical probes are used to treat a variety of diseases. The cryosurgical probes quickly freeze diseased body tissue, causing the tissue to die after which it will be absorbed by the body or expelled by the body. Cryothermal treatment is currently used to treat prostate cancer and benign prostate disease, breast tumors and breast cancer, liver tumors and cancer, glaucoma and other eye diseases. Cryosurgery is also proposed for the treatment of a number of other diseases.

The use of cryosurgical probes for cryoablation of the uterus is described in Cahan, W. G. and Brockunier, A., *Cryosurgery of the Uterine Cavity.* Am. Obstet. Gynec. 99:138–153, 1967. Cahan and Brockunier describe a cryosurgical probe patterned after the curve and diameter of a No. 6 Hegar dilator. Liquid nitrogen circulates through this cryosurgical probe in order to cause cryonecrosis of the diseased endometrial tissue in the uterus. Multiple applications of freezing and thawing are applied using the curved probe in order to treat left and right cornu of the uterus as well as the fundus. This method of cryosurgery has a number of drawbacks because the uterus has, for example, an irregular shape resulting from the left and right cornu. Moreover, the uterus has a rough and irregular lining which is not amenable to efficient cryosurgery. Because of the irregular shape and rough lining of the uterus, a clinician will often miss a portion of diseased tissue and must subject the patient to multiple sessions of cryosurgery. In addition, should the cryoprobe perforate the uterus, life-threatening or fatal hemorrhage may result because of the highly vascular nature of the uterine lining.

Precise positioning of the cryoprobe is thus vital to prevent perforation or unnecessary multiple sessions of cryosurgery. Typically, a clinician monitors the position of the cyroprobe within the uterus by using an ultrasound probe inserted in the rectum or through an external ultrasound transducer. Alternatively, the clinician may monitor the position of the cryoprobe through imaging with x-rays. Monitoring the position of the cyroprobe with such means, however, suffers from a number of drawbacks. For example, a clinician examining ultrasound and x-ray images will have difficulty in distinguishing uterine tissue from the surrounding organs. The clinician would much prefer positioning the cryoprobe under direct vision rather than using such indirect means. There is a need in the art for better techniques in positioning a cryoprobe before ablation. Other ablation devices such as microwave ablation needles also require precise positioning. The present invention addresses this need in the art.

SUMMARY OF THE INVENTION

In one innovative aspect, a placement guide in accordance with the present invention comprises an outer catheter and an inner tubular member. The outer catheter has a proximally located seat capable of engaging a stop on an ablation device which extends distally a first predermined distance from the stop. The outer catheter extends distally a second predetermined distance from the proximally located seat and has a lumen sized to accommodate an ablation device for movement therein. Because the second predetermined distance is less than the first predetermined distance, the ablation device extends from the distal end of the outer catheter when the ablation device is inserted into the lumen of outer catheter so that the stop and the proximally located seat are engaged.

The inner tubular member, which is preferably closed at its distal end, extends distally the first predetermined distance from a proximally located stop formed to engage the proximally located seat on the outer catheter. The inner tubular member has a port at its proximal end and a lumen of appropriate size to accommodate an endoscope. In a preferred embodiment, the stop comprises a handle mounted on the proximal end of the inner tubular member, and the seat on the outer catheter comprises a handle on the outer sheath's proximal end.

In another innovative aspect, the present invention is directed to methods of positioning an ablation device within a patient using the above-described outer catheter and inner tubular member. With the stop of the inner tubular member engaging the seat on the proximal portion of the outer catheter, the clinician positions the distal end of the inner tubular member under direct vision through an endoscope inserted within the inner tubular member's lumen so that the distal end is optimally located for later ablation. The clinician secures the outer catheter in position relative to the patient and withdraws the inner tubular member. A cryoprobe is inserted into the secured-in-place outer catheter until it engages the outer catheter's seat whereby the cryoprobe has a distal projection which extends from the distal end of the outer catheter. Because both the inner tubular member's distal projection and the cryoprobe's distal projection have the same length, the distal end of the cryoprobe is located where the inner tubular member's distal end was previously positioned so that ablation may begin in an optimal location.

BRIEF DESCRIPTION OF THE DRAWINGS

FIG. 1 is a side-elevational view of the placement guide according to one embodiment of the invention.

FIG. 2 is a view of the placement guide positioned in a uterus using an endoscope according to one embodiment of the invention.

DETAILED DESCRIPTION OF THE PREFERRED EMBODIMENTS

Figure 3:
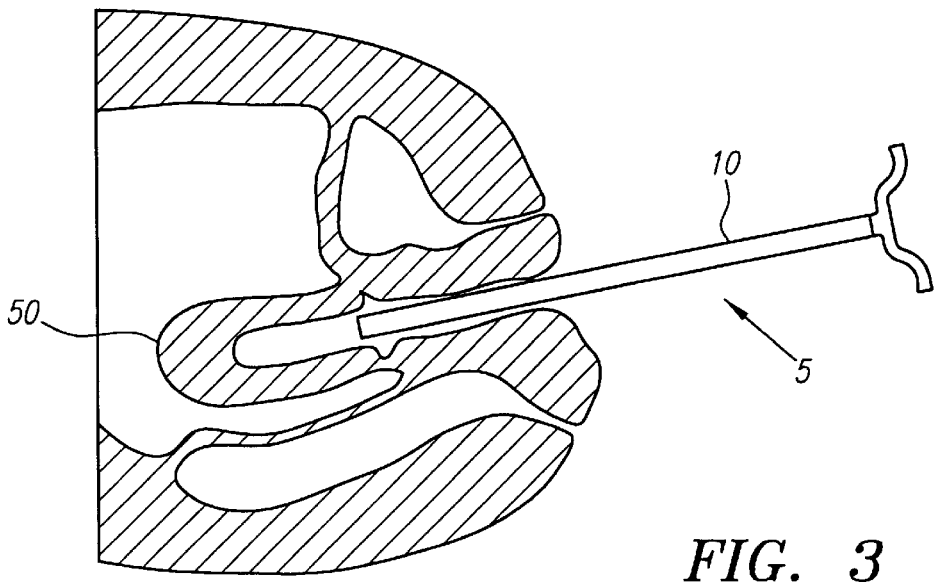
FIG. 3 is a view of the placement guide positioned in a uterus with the inner tubular member withdrawn according to one embodiment of the invention.

Turning now to the drawings, FIG. 1 shows a placement guide 5 for a surgical albation device according to one embodiment of the invention. An outer catheter 10 slidably engages within its lumen an inner tubular member 15. Outer catheter 10 and inner tubular member 15 may be constructed from medical grade polycarbonate, glass, polyurethane, etc.

In addition, inner tubular member 15 and outer catheter 10 may be doped with lead or other radiopaque materials to assist imaging of the placement guide 5 with x-rays. Inner tubular member 15 possesses a lumen adequate to accommodate an endoscope 45 (illustrated in FIG. 2), and the endoscope may be inserted into the lumen of the inner tubular member 15 via a port (not illustrated) provided at the proximal end of the inner tubular member 15.

The inner tubular member 15 may be distally displaced within the lumen of the outer catheter 10 until a stop 20 on the inner tubular member 15 abuts a seat 25 on the outer catheter 10. The stop 20 preferably will comprise a handle 30 located on the proximal end of the inner tubular member 15. Similarly, the seat 25 preferably will comprise a handle 35 located on the proximal end of the outer catheter 10 wherein the handles 30 and 35 are configured to closely mesh together. It is evident to one of ordinary skill in the art, however, that many alternate structures may be used to form the stop 20 and seat 25. When the inner tubular member 15 is distally displaced so that the handles 30 and 35 abut one another, a distal projection 40 of the inner tubular member 15 extends from the distal end of the outer catheter 10 (shown partially extended in FIG. 1). The distal projection 40 preferably is made entirely of optically transparent material to facilitate imaging through an endoscope 45 (illustrated in FIG. 2) inserted in the lumen of the inner tubular member 15 through a port at the proximal end of the inner tubular member. The inner tubular member 15 preferably is closed at its distal end where a lens (not illustrated) may optionally be used to further facilitate imaging through the inserted endoscope 45. Fluid ports (not illustrated) may optionally be used to fill the lumen of the inner tubular member 15 with saline or other fluids to assist imaging through the inserted endoscope 45.

Figure 4:
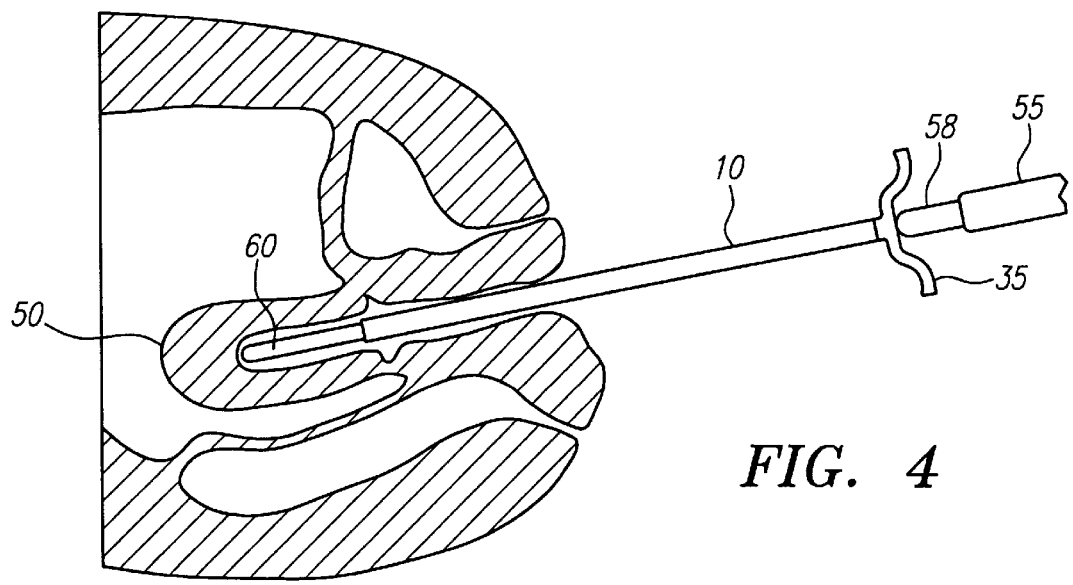
FIG. 4 is a view of a cryoprobe inserted into a uterus through the outer catheter of the placement guide according to one embodiment of the invention.

Turning now to FIGS. 2 through 5, a method of positioning an ablation device using the placement guide 5 is illustrated. Although these figures illustrate a method of positioning a cryoprobe, those of ordinary skill in the art will appreciate that the placement guide 5 could also position other types of ablation devices such as a microwave ablation needle or thermal ablation devices. Moreover, although a method of uterine ablation is outlined, the invention may be used to guide ablation devices to treat liver tumors, prostatatic tumors or hyperplasia, etc. By imaging through an endoscope 45 inserted in the lumen of the inner tubular member 15, the clinician guides the placement device 5 into proper position into the uterus 50. The inner tubular member 15 is distally displaced in the lumen of the outer catheter 10 so that the handles 30 and 35 abut each other, preventing further distal displacement of the inner tubular member 15. Using the endoscope 45, the clinician verifies that the distal projection 40 of the inner tubular member 15 is optimally located for later cryoablation. The clinician's view though the endoscope 45 may be aided through a lens optionally located at the distal end of the inner tubular member 15. In addition to locating the distal projection 40 under direct vision using the endoscope 45, the clinician may also indirectly monitor the location of the distal projection 40 through, for example, ultrasound or x-ray imaging. When satisfied with the placement of the distal projection 40, the clinician may withdraw the inner tubular member 15 with its endoscope 45 from the outer catheter 10 as illustrated in FIG. 3. The outer catheter is secured in position with respect to the uterus 50 during and subsequent to this withdrawal, either manually or with a securing means such as a clamp or tape. As illustrated in FIG. 4, an ablation device such as cryoprobe 55 replaces inner tubular member 15 within the lumen of the outer catheter 10. Similar to the inner tubular member 15, the cryoprobe 15 has an annular region 58 that functions as a stop to abut against the seat 25 of the outer catheter 10 (in this embodiment, the handle 35) to prevent further distal displacement within the lumen of the outer catheter 15 whereby a distal projection 60 of the cyroprobe extends from the distal end of the outer catheter 10.

Figure 5:
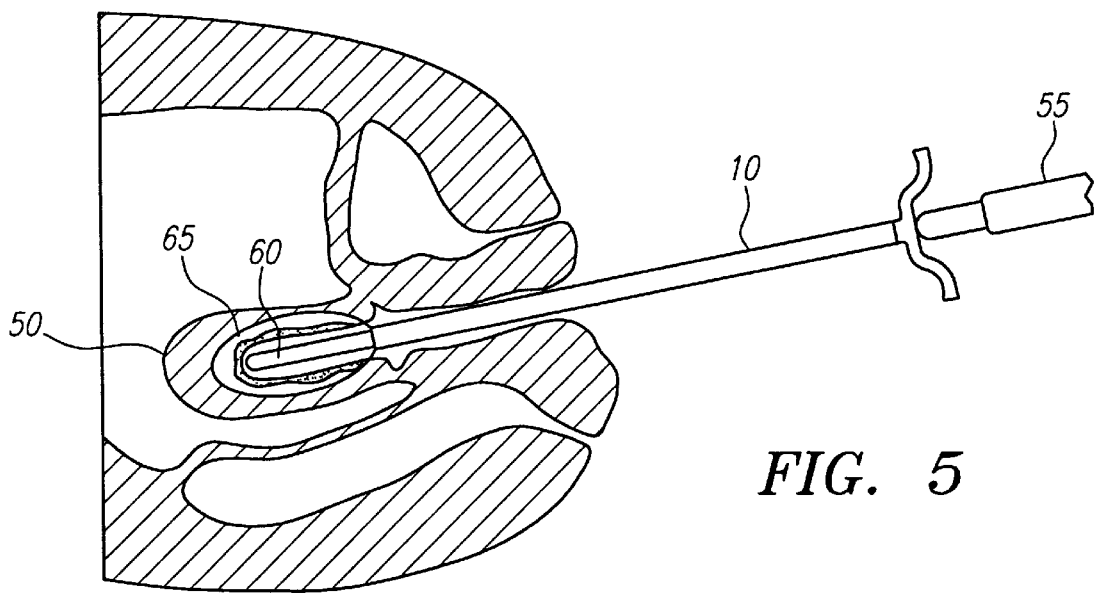
FIG. 5 is a view of a cryoprobe inserted through the outer catheter of the placement guide wherein the cyroprobe has performed uterine ablation according to one embodiment of the invention.

It is to be noted that the length of the inner tubular member as defined between its distal end and the stop 20 is chosen such that the length of the inner tubular member's distal projection 40 is substantially identical to the length of the cryoprobe's distal projection 60. Therefore, if the cryoprobe 55 is distally displaced in the outer catheter 10 such that the annular region 58 abuts against the handle 35, the distal projection 60 is located where the inner tubular member's distal projection 40 had been because the outer catheter 10 was secured in position with respect to the uterus 50. Because the clinician had positioned the inner tubular member's distal projection under direct vision using an endoscope 45, the cryoprobe's distal projection 60 is optimally located within the uterus 50 for cryoablation. Turning now to FIG. 5, the clinician activates the cryoprobe 55 to form an iceball 65 within the uterus to complete the cryoablation. The present invention allows the clinician to know that the iceball 65 will be formed in an optimal location. Although it is to be expected that the cyroprobe 55 will be optimally placed given that the outer catheter 10 has been fixed in position with respect to the uterus 50, the clinician may monitor the position of the cryoprobe though ultrasound or x-ray imaging prior to beginning ablation. Such imaging, in particular ultrasound imaging, would also allow the clinician to monitor the resulting size of the iceball 65.

Although the placement guide 5 is particularly useful for positioning a cryoprobe 55 for endometrial ablation because of the highly vascular nature of the uterus, cryosurgery on other organs in the body will also benefit from the added safety of this invention. Moreover, the benefits provided by the placement guide 5 may be used to guide the placement of other types of ablation devices for safe and effective ablation. Thus, while the preferred embodiments of the devices and methods have been described in reference to the environment in which they were developed, they are merely illustrative of the principles of the invention. Other embodiments and configurations may be devised without departing from the spirit of the invention and the scope of the appended claims.

What is claimed is:

1. A placement guide comprising:

an ablation device that extends distally a first predetermined distance from a stop;

an outer catheter having a lumen and a proximally located seat; said lumen sized to allow movement of the ablation device therein, wherein said proximally located seat of said outer catheter is adapted to engage the stop of the ablation device, and wherein said outer catheter extends distally from said proximally located seat a second predetermined distance, said second predetermined distance being less than the first predetermined distance; and an inner tubular member formed for movement within the lumen of said outer catheter, said inner tubular member having a proximally located stop for engaging said seat, said inner tubular member extending the first predetermined distance from said proximally located stop, said inner tubular member having a lumen sized to accommodate an endoscope.

2. The device of claim 1 wherein the stop of said inner tubular member comprises a handle, and wherein the seat of said outer catheter comprises a handle.

3. The device of claim 1 wherein at least said inner tubular member is doped with a radiopaque material.

4. The device of claim 1 wherein said inner tubular member further comprises a lens located at the distal end of said inner tubular member wherein imaging through an endoscope inserted within said lumen of said inner tubular member is facilitated.

5. The device of claim 1 wherein said inner tubular member comprises an optically clear material.

6. The device of claim 1 wherein the inner tubular member further comprises a fluid port for flooding the lumen of the inner tubular member to facilitate endoscopic imaging.

7. A method of positioning an ablation device using a placement guide, wherein the ablation device extends distally a first predetermined distance from a stop, said method comprising the steps of:

providing a placement guide comprising:
  an outer catheter having a lumen and a proximally located seat; said lumen sized to allow movement of the ablation device therein, wherein said proximally located seat of said outer catheter is adapted to engage the stop of the ablation device and wherein said outer catheter extends distally from said proximally located seat a second predetermined distance, said second predetermined distance being less than the first predermined distance, and
  an inner tubular member formed for movement within the lumen of said outer catheter, said inner tubular member having a proximally located stop for engaging said seat, said inner tubular member extending the first predetermined distance from said proximally located stop, said inner tubular member having a lumen sized to accommodate an endoscope;
 inserting said inner tubular member into said lumen of said outer catheter so that said stop of said inner tubular member engages said seat of said outer catheter;
 positioning in a human body the distal end of said inner tubular under direct vision using an endoscope inserted in said lumen of said inner tubular while said stop of said inner tubular member engages said seat of said outer catheter;
 securing said outer catheter in position with respect to the human body;
 withdrawing said inner tubular member from said outer catheter;
 inserting the ablation device into said outer catheter so that the stop of the ablation device engages said outer catheter's seat; and
 performing ablation within the human body using the ablation device.

8. The method of claim 7 wherein said ablation device is a cryoprobe and wherein said step of performing ablation causes an iceball to be formed within the human body.

9. The method of claim 7 wherein said positioning step further comprises imaging said distal projection of said inner tubular member with x-rays.

10. The method of claim 7 further comprising the step of:
 monitoring the formation of the iceball using ultrasound imaging.

* * * * *